(12) United States Patent
Mikulásik et al.

(10) Patent No.: US 9,775,908 B2
(45) Date of Patent: Oct. 3, 2017

(54) PHARMACEUTICAL PREPARATIONS CONTAINING HIGHLY VOLATILE SILICONES

(75) Inventors: Endre Mikulásik, Alsónemesapáti (HU); Patrik Fazekas, Körmend (HU)

(73) Assignee: EGIS GYOGYSZERGYAR NYILVANOSAN MUKODO RESZVENYTARSASAG, Budapest (HU)

( * ) Notice: Subject to any disclaimer, the term of this patent is extended or adjusted under 35 U.S.C. 154(b) by 650 days.

(21) Appl. No.: 12/672,696

(22) PCT Filed: Jul. 10, 2008

(86) PCT No.: PCT/HU2008/000083
§ 371 (c)(1),
(2), (4) Date: Apr. 9, 2010

(87) PCT Pub. No.: WO2009/007764
PCT Pub. Date: Jan. 15, 2009

(65) Prior Publication Data
US 2010/0215756 A1     Aug. 26, 2010

(30) Foreign Application Priority Data
Jul. 10, 2007   (HU) .................................. 0700473

(51) Int. Cl.
*A61K 9/14*     (2006.01)
*A61K 31/522*   (2006.01)
(Continued)

(52) U.S. Cl.
CPC ............. *A61K 47/34* (2013.01); *A61K 9/06* (2013.01); *A61K 31/4164* (2013.01);
(Continued)

(58) Field of Classification Search
None
See application file for complete search history.

(56) References Cited

U.S. PATENT DOCUMENTS 3,998,973 A   12/1976 Carlson
4,831,023 A    5/1989 Desai et al.
(Continued)

FOREIGN PATENT DOCUMENTS

DE   2704081 A1   8/1977
DE   3805744 A1   9/1988
(Continued)

OTHER PUBLICATIONS

Karade, Preeti, "Formulation and Evaluation of Celecoxib Gel," http://www.jddtonline.info/index.php/jddt/article/view/148, Journal of Drug Delivery and Therapeutics, May 2012, vol. 2, Issue 3.
(Continued)

*Primary Examiner* — Bethany Barham
*Assistant Examiner* — Dominic Lazaro
(74) *Attorney, Agent, or Firm* — Knobbe, Martens, Olson & Bear LLP

(57) ABSTRACT

The subject of the present invention is a transdermal preparation containing pharmaceutically active ingredient, wherein the particles of the active ingredient are coated with highly volatile silicones or a mixture thereof, and these coated particles are dispersed in a gel or cream base. The volatile silicone component is hexamethyldisiloxane and/or octamethyltrisiloxane and/or decamethylpentacyclo-siloxane. A further subject of the present invention is a method for the preparation of such pharmaceutical compositions.

36 Claims, 11 Drawing Sheets

(51) Int. Cl.

| | |
|---|---|
| *A61K 31/5415* | (2006.01) |
| *A61K 31/19* | (2006.01) |
| *A61K 31/195* | (2006.01) |
| *A61K 31/4164* | (2006.01) |
| *A61K 31/44* | (2006.01) |
| *A61K 31/04* | (2006.01) |
| *A61K 31/495* | (2006.01) |
| *A61P 37/08* | (2006.01) |
| *A61P 31/04* | (2006.01) |
| *A61K 47/34* | (2017.01) |
| *A61K 9/06* | (2006.01) |
| *A61K 47/02* | (2006.01) |
| *A61K 31/4174* | (2006.01) |
| *A61K 9/00* | (2006.01) |
| *A61K 9/16* | (2006.01) |

(52) U.S. Cl.
CPC ........ *A61K 31/4174* (2013.01); *A61K 31/495* (2013.01); *A61K 31/5415* (2013.01); *A61K 47/02* (2013.01); A61K 9/0014 (2013.01); A61K 9/1611 (2013.01)

(56) References Cited

U.S. PATENT DOCUMENTS

| | | |
|---|---|---|
| 4,837,019 A | 6/1989 | Deckner et al. |
| 5,122,519 A | 6/1992 | Ritter |
| 5,210,103 A | 5/1993 | Grace et al. |
| 5,374,661 A * | 12/1994 | Betlach, II ............ 514/772.4 |
| 5,451,405 A | 9/1995 | Bartolone et al. |
| 5,466,823 A | 11/1995 | Bertenshaw et al. |
| 5,504,215 A | 4/1996 | Talley et al. |
| 5,508,426 A | 4/1996 | Talley et al. |
| 5,510,496 A | 4/1996 | Talley et al. |
| 5,516,907 A | 5/1996 | Talley et al. |
| 5,521,207 A | 5/1996 | Graneto |
| 5,563,165 A | 10/1996 | Talley et al. |
| 5,698,589 A | 12/1997 | Allen |
| 5,756,109 A | 5/1998 | Burger et al. |
| 5,851,544 A | 12/1998 | Habif et al. |
| 6,007,829 A | 12/1999 | Burger et al. |
| 6,156,781 A | 12/2000 | Talley et al. |
| 6,361,806 B1 | 3/2002 | Allen |
| 6,375,986 B1 | 4/2002 | Ryde et al. |
| 6,413,960 B1 | 7/2002 | Talley et al. |
| 6,589,557 B2 | 7/2003 | Straub et al. |
| 6,592,903 B2 | 7/2003 | Ryde et al. |
| 6,800,297 B2 | 10/2004 | Altreuter et al. |
| 7,138,394 B2 | 11/2006 | Schwarz et al. |
| 7,387,789 B2 | 6/2008 | Klose et al. |
| 7,781,429 B2 | 8/2010 | Schwarz et al. |
| 8,246,976 B2 | 8/2012 | Nguyen |
| 2002/0013300 A1 | 1/2002 | Capelli-Schellpfeffer |
| 2002/0110597 A1 | 8/2002 | Ruddy et al. |
| 2003/0104019 A1 | 6/2003 | Hopkins et al. |
| 2003/0161867 A1 | 8/2003 | Lu et al. |
| 2003/0180281 A1 | 9/2003 | Bott et al. |
| 2003/0199537 A1 | 10/2003 | Cannon et al. |
| 2004/0029946 A1 | 2/2004 | Arora et al. |
| 2004/0033267 A1 | 2/2004 | Merisko-Liversidge et al. |
| 2004/0063794 A1 | 4/2004 | Schwarz et al. |
| 2004/0120918 A1 | 6/2004 | Lintner et al. |
| 2005/0032916 A1 | 2/2005 | Deckner |
| 2005/0049291 A1 | 3/2005 | Kumar et al. |
| 2005/0069566 A1* | 3/2005 | Tamarkin et al. ............ 424/401 |
| 2005/0074487 A1 | 4/2005 | Hsu et al. |
| 2005/0096371 A1 | 5/2005 | Krishnan et al. |
| 2005/0158348 A1 | 7/2005 | Schwarz et al. |
| 2005/0202056 A1 | 9/2005 | Hopkins et al. |
| 2005/0255130 A1 | 11/2005 | Vishnupad et al. |
| 2005/0255131 A1 | 11/2005 | Vishnupad et al. |
| 2005/0255133 A1 | 11/2005 | Schwarz et al. |
| 2005/0266061 A1 | 12/2005 | Stinchcomb et al. |
| 2006/0015058 A1 | 1/2006 | Kellogg et al. |
| 2006/0159648 A1 | 7/2006 | Davis et al. |
| 2006/0188557 A1 | 8/2006 | Ikesue et al. |
| 2006/0211688 A1 | 9/2006 | Schwarz et al. |
| 2006/0241175 A1 | 10/2006 | Schwarz et al. |
| 2007/0036731 A1* | 2/2007 | Hirsh et al. ............ 424/46 |
| 2007/0269393 A1 | 11/2007 | Wepfer |
| 2008/0050461 A1 | 2/2008 | Merisko-Liversidge et al. |
| 2008/0107741 A1 | 5/2008 | Merisko-Liversidge et al. |
| 2008/0226732 A1 | 9/2008 | Merisko-Liversidge et al. |
| 2008/0279949 A1 | 11/2008 | Merisko-Liversidge et al. |
| 2010/0105750 A1 | 4/2010 | Aksamit et al. |
| 2010/0215756 A1 | 8/2010 | Mikulasik et al. |
| 2010/0233272 A1 | 9/2010 | Appel et al. |
| 2010/0266692 A1 | 10/2010 | Bloom et al. |
| 2010/0322852 A1 | 12/2010 | Merisko-Liversidge et al. |
| 2010/0322853 A1 | 12/2010 | Merisko-Liversidge et al. |
| 2010/0323014 A1 | 12/2010 | Bloom et al. |
| 2010/0329976 A1 | 12/2010 | Bosch et al. |
| 2012/0004305 A1 | 1/2012 | Miura et al. |
| 2012/0004306 A1 | 1/2012 | Miura et al. |

FOREIGN PATENT DOCUMENTS

| | | |
|---|---|---|
| DE | 4131678 A1 | 10/1992 |
| DE | 19700913 A1 | 7/1998 |
| DE | 10032132 A1 | 1/2002 |
| DE | 102004043112 A1 | 3/2006 |
| EP | 0176217 A1 | 4/1986 |
| EP | 0288734 A1 | 11/1988 |
| EP | 0328806 A2 | 8/1989 |
| EP | 0579455 A1 | 1/1994 |
| EP | 0 639 372 | 2/1995 |
| EP | 0914082 A1 | 5/1998 |
| EP | 1296679 B1 | 3/2006 |
| FR | 2471778 A1 | 6/1981 |
| FR | 2862871 A1 | 6/2005 |
| GB | 2050160 A | 1/1981 |
| GB | 2144989 A | 3/1985 |
| GB | 2185269 A | 7/1987 |
| JP | H02-145512 | 6/1990 |
| JP | 2004-075592 A | 3/2004 |
| JP | 2009-280509 | 12/2009 |
| KR | 2001018961 A | 3/2001 |
| WO | WO 84/01710 A1 | 5/1984 |
| WO | WO 95/03805 A1 | 2/1995 |
| WO | WO 95/17162 A1 | 6/1995 |
| WO | WO 95/23596 A1 | 9/1995 |
| WO | WO 96/20699 A1 | 7/1996 |
| WO | WO 96/27372 A1 | 9/1996 |
| WO | WO 97/10196 A1 | 3/1997 |
| WO | WO 97/44008 A1 | 11/1997 |
| WO | WO 97/45123 A1 | 12/1997 |
| WO | WO 98/05299 A1 | 2/1998 |
| WO | WO 98/10768 A1 | 3/1998 |
| WO | WO 98/13017 A1 | 4/1998 |
| WO | WO 98/17252 | 4/1998 |
| WO | WO 98/30244 A1 | 7/1998 |
| WO | WO 98/53795 A1 | 12/1998 |
| WO | WO 99/13855 A1 | 3/1999 |
| WO | WO 99/22703 A1 | 5/1999 |
| WO | WO 99/24000 A2 | 5/1999 |
| WO | WO 99/24006 A1 | 5/1999 |
| WO | WO 99/30678 A1 | 6/1999 |
| WO | WO 00/07566 A1 | 2/2000 |
| WO | WO 00/07627 A2 | 2/2000 |
| WO | WO 00/37040 A1 | 6/2000 |
| WO | WO 00/59465 A1 | 10/2000 |
| WO | WO 00/64450 A1 | 11/2000 |
| WO | WO 01/43722 | 6/2001 |
| WO | WO 01/56576 A1 | 8/2001 |
| WO | WO 02/02111 A1 | 1/2002 |
| WO | WO 02/17889 A1 | 3/2002 |
| WO | WO 02/39960 A2 | 5/2002 |
| WO | WO 02/41865 A1 | 5/2002 |
| WO | WO 02/41866 A2 | 5/2002 |
| WO | WO 02/017928 A2 | 7/2002 |
| WO | WO 03/013462 A1 | 2/2003 |
| WO | WO 03/055465 A1 | 7/2003 |

(56) References Cited

FOREIGN PATENT DOCUMENTS

| | | |
|---|---|---|
| WO | WO 03/061721 A1 | 7/2003 |
| WO | WO 03/086331 A2 | 10/2003 |
| WO | WO 2004/092283 A2 | 10/2004 |
| WO | WO 2004/096169 A1 | 11/2004 |
| WO | WO 2005/000248 A2 | 1/2005 |
| WO | WO 2005/007129 A2 | 1/2005 |
| WO | WO 2005/046600 A2 | 5/2005 |
| WO | WO 2006/028863 A1 | 3/2006 |
| WO | WO 2006/031848 A2 | 3/2006 |
| WO | WO 2006/091297 A2 | 8/2006 |
| WO | WO 2006/138035 | 12/2006 |
| WO | WO 2007/051596 A1 | 5/2007 |
| WO | WO 2007/066889 A1 | 6/2007 |
| WO | WO 2007/070983 A1 | 6/2007 |
| WO | WO 2009/031318 | 3/2009 |
| WO | WO 2010/103845 | 9/2010 |

OTHER PUBLICATIONS

Mansour, S., "Preparation and evaluation of topical dibucaine emulsion gels," From Egyptian Journal of Biomedical Sciences, 2007, 24, 1-21.
Mackie et al., "Effect of the interfacial layer composition on the properties of emulsion creams," Journal of Agricultural and Food Chemistry, 2007, 55(14), 5611-5619.
Park et al., "Formulation design and evaluation of a ursolic acid microemulsion delivery system for topical formulation," Yakche Hakhoechi, 2005, 35(4), 233-241.
Moates et. al., "Creaming and oscillation rheology of weakly flocculated concentrated emulsions," Colloids and Surfaces, A: Physicochemical and Engineering Aspects, 2001, 190(1-2), 167-178.
Williams et al., "Scale-up of an oil/water cream containing 40% diethylene glycol monoethyl ether," Drug Development and Industrial Pharmacy (2000), 26(1), 71-77.
Manoj et al., "Creaming and rheology of flocculated emulsions," ACS Symposium Series, 1999, 737(Polysaccharide Applications), 234-251.
Wang et al., "The effect of rheological properties of experimental moisturizing creams/lotions on their efficacy and perceptual attributes," International Journal of Cosmetic Science, 1999, 21(3), 167-188.
Manoj et al., "Characterization of a depletion-flocculated polydisperse emulsion. I. Creaming behavior," Journal of Colloid and Interface Science, 1998, 207(2), 283-293.
Fuehrer et al., "Structural research and manufacturing practice of semisolid preparations," SOFW Journal, 1996, 122(10), 664,666,669-670.
Tiemessen et al., "Probing the microstructure of liquid crystalline surfactant systems; a physicochemical study using the rheometry, DTA and oxygen-17 NMR," Journal of Controlled Release, 1990, 13(1), 73-81.
Mueller-Goymann, "Microstructure of 4-component creams," Acta Pharmaceutica Technologica, 1989, 35(3), 116-20.
Tiemessen et al., "In vitro drug release from liquid-crystalline creams; cream structure dependence," Progress in Colloid & Polymer Science, 1988, 77(Dispersed Syst.), 131-5.
Madsen, W. Soendergaard, "Chlorhexidine," Journal of Hospital Pharmacy, 1969, 26(2), 53-5.
Tichy et al., "Effect of β-(1,3)-glucan on rheological properties and stability of topical formulations," Pharmazie, 2006, 61(12), 1050-1051.
Biruss et al., "Evaluation of an eucalyptus oil containing topical drug delivery system for selected steroid hormones," International Journal of Pharmaceutics, 2007, 328(2), 142-151.
Csoka et al., "In vitro and in vivo percutaneous absorption of topical dosage forms: case studies," International Journal of Pharmaceutics, 2005, 291(1-2), 11-19.
Csoka et al., "In vitro drug release and in vivo percutaneous absorption studies of topical dosage forms," Farmacevtski Vestnik, 2003, 54(Spec. Issue), 347-348.
Nour et al., "Formulation and evaluation of econazole nitrate emulgels," Journal of Drug Research, 2002, 24(1-2), 63-71.
El Laithy et al., "The development of cutina lipogels and gel microemulsion for topical administration of fluconazole," AAPS PharmSciTech (2002), 3(4).
Huhtala et al., "A Collaborative Evaluation of the Cytotoxicity of Two Surfactants by Using the Human Corneal Epithelial Cell Line and the WST-1 Test," Journal of Ocular Pharmacology and Therapeutics, 2003, 19(1), 11-21.
Schlesinger, Marcia, "Topical aerosol foam formulations," Cosmetics & Toiletries, 2000, 115(8), 67-70.
Memisoglu et al., "In vivo evaluation for rhGM-CSF wound-healing efficacy in topical vehicles," Pharmaceutical Development and Technology, 1997, 2(2), 171-180.
Wang et al., "Effect of various physical/chemical properties on the transdermal delivery of cyclosporin through topical application," Drug Development and Industrial Pharmacy, 1997, 23(1), 99-106.
Tous et al., "Acetazolamide topical formulation and ocular effect," S.T.P. Pharma Sciences, 1992, 2(1), 125-31.
Wepierre et al., "Irritant effects of surface active agents evaluated by measuring skin blood flow in the guinea pig," Labo-Pharma—Problemes et Techniques, 1977, 25(264), 300-3.
Modi et al., "A comparative solubility enhancement profile of valdecoxib with different solubilization approaches," Indian Journal of Pharmaceutical Sciences, 2007, 69(2), 274-278.
Abou-Taleb et al., "Formulation and stability of rofecoxib suppositories," Journal of Drug Delivery Science and Technology, 2006, 16(5), 389-396.
Lu et al., "Transdermal and lymph targeting transfersomes of vincristine," Yaoxue Xuebao, 2007, 42(10), 1097-1101.
Junyaprasert et al., "Transdermal delivery of hydrophobic and hydrophilic local anesthetics from o/w and w/o Brij 97-based microemulsions," Journal of Pharmacy & Pharmaceutical Sciences, 2007, 10(3), 288-298.
Valiveti et al., "Transdermal permeation of WIN 55,212-2 and CP 55,940 in human skin in vitro," International Journal of Pharmaceutics, 2004, 278(1), 173-180.
Lee et al., "Evaluation of various vehicles and O/W microemulsions of flurbiprofen as transdermal delivery system," Yakche Hakhoechi, 1998, 28(3), 141-149.
Bodde et al., "Hydrogel patches for transdermal drug delivery; in vivo water exchange and skin compatibility," Journal of Pharmacy and Pharmacology, 1989, 41(3), 152-5.
International Written Opinion for International Application No. PCT/HU2008/000083, Date of Opinion issuance Jan. 10, 2010, 13 pages.
International Preliminary Report on Patentability for International Application No. PCT/HU2008/000083, Date of Preliminary Report issuance Jan. 10, 2010, 14 pages.
Hungarian Office Action for Hungarian Patent Application No. HU20070000473 dated May 9, 2012.
English Translation of Hungarian Office Action for Hungarian Patent Application No. HU20070000473 dated May 9, 2012.
Notice on the Publication of the Patent Application and the Completion of a Novelty Search for Hungarian Patent Application No. HU20070000473 dated on Sep. 23, 2009.
English Translation of Notice on the Publication of the Patent Application and the Completion of a Novelty Search for Hungarian Patent Application No. HU20070000473 dated on Sep. 23, 2009.
Yener, G., et al., "Effect of vehicles and penetration enhancers on the in vitro percutaneous absorption of celecoxib through human skin," Pharmazie, May 2003, 58(5): 330-3; abstract only provided.
Soliman, S., et al., "Formulation of microemulsion gel systems for transdermal delivery of celecoxib: In vitro permeation, anti-inflammatory activity and skin irritation tests," Drug Discoveries & Therapeutics, 2010, 4(6), pp. 459-471.
Lieberman, H.A., "Pharmaceutical dosage forms: disperse systems," 1996, Edition 2, vol. 2, p. 251.

(56) References Cited

OTHER PUBLICATIONS

Dorland's Medical Dictionary for Healthcare Consumers, 2007, Elsevier, Definition of "transdermal" in 1 page.

* cited by examiner

PHARMACEUTICAL PREPARATIONS CONTAINING HIGHLY VOLATILE SILICONES

CROSS REFERENCE TO RELATED APPLICATIONS

This application is the US national phase of PCT application PCT/HU2008/000083, filed 10 Jul. 2008, published 15 Jan. 2009 as WO2009/007764, and claiming the priority of Hungarian patent application P0700473 itself filed 10 Jul. 2007, whose entire disclosures are herewith incorporated by reference.

FIELD OF THE INVENTION

This invention relates to a transdermal preparation containing a pharmaceutically active ingredient, wherein the particles of the active ingredient are coated with highly volatile silicones or a mixture thereof and these coated particles are dispersed in a gel or cream base. This invention further relates to a method for the preparation of such pharmaceutical compositions.

BACKGROUND OF THE INVENTION

The application of the silicone derivatives in medicine started in the 1930's and since then they have been applied extensively.

As to the group of silicone derivatives, the application of silicone polymers are really widespread in the field of pharmaceutics, because they have several advantageous characteristics, such as high flexibility, heat-resistance, beneficial chemical resistance, they are indifferent to the human organism, they have no interaction with it in the course of pharmaceutical application.

Silicone polymers—polyorganosiloxanes—are polymer compounds, wherein organic chemical groups are attached to the siloxane chains (—Si—O—Si—).

By the hydrolysis or condensation of chlorosilane monomers different silicone polymers can be prepared. These polymers have three main groups depending on their structures:
  silicone oils and natural elastomers with linear structure,
  silicone resins with branched structure,
  silicone resins with cross-linked structure (most of the silicone resins have cross-linked structure).

Not only silicone oils with different degree of viscosity but also fat silicones, antifoams, form release agents and hydrophobizing agents can be prepared from the silicone polymers. Silicone rubbers are prepared from silicon caoutchoucs by different vulcanizing and cross-linking processes.

Resins can be used as pressing powders, pressing resins, resin emulsions, lacquers (solutions with different solvents) and pigmented paints or resins modified with organic components.

Silicone polymers are important basic materials of the pressure sensitive adhesives (PSA), medicinal and surgical implants, prostheses used in the therapy and different transdermal therapeutic systems (TTS).

Among the silicone oils dimethyl polysiloxanes are applied most often in the therapy. These silicone oils have very strong antifoaming properties, which arise from their low surface tension (approximately 20 mN/m, for comparison the surface tension of water is 85 mN/m). This advantage is employed by the application of silicone oil in sprays for the treatment of lung oedema. In case of lung oedema the strongly foamy mucus originating from the lung and malting a barrier in the normal ventilation and in the oxygen uptake can cause anoxia or suffocation in lack of treatment. The hydrophobic characteristics of silicone oils are used in pharmaceutical preparations for the treatment of bedsore and ulcer with patients who have to stay in a single decubitus position for a lengthy period.

One sub-group of silicone oils are the highly volatile silicones. The highly volatile silicones are pharmaceutical carriers which are able to evaporate completely from the surface of the human skin within 6 hours. The pharmaceutical use of these carriers has not been exhausted every possibility, yet.

The subject of the present invention is a pharmaceutical transdermal preparation, wherein the particles of the active ingredient are coated with hexamethyldisiloxane, octamethyltrisiloxane and decamethylpentacyclosiloxane. These highly volatile silicone oils are widely used in the cosmetics industry and their pharmaceutical application is also known.

U.S. Pat. Nos. 4,355,046 and 5,336,692 describe the use of hexamethyldisiloxane, octamethyltrisiloxane and decamethylpentacyclosiloxane solvents in ointments having a petrolatum base. The ointments are applied in cosmetics and medicine. According to these patents highly volatile siloxanes serve exclusively in order to obtain a good distribution on the surface of the human skin, but not to attain chemical and microbiological stability. The type and the composition of the pharmaceutical preparations and also the ointment base cited in the descriptions are different from the subject of the present invention. In U.S. Pat. No. 5,210,103 hexamethyldisiloxane is used as power gas in skin foams for external use (for example: vaginal).

European Patent No. EP 914082 relates to an antiperspirant composition containing volatile siloxanes. These silicones assure the suitable consistency of the composition and avoid any leakage of the product from the packaging.

By the production of Diprolene Creme® (Schering Plough) and Dexeryl Creme® (Pierre Fabre Sante) decamethylpentacyclosiloxane is used to assure the aesthetics of the product.

All of the above cited documents describe cosmetic compositions wherein the volatile siloxanes are used to assure the suitable consistency of the compositions and the aesthetics of the products.

Volatile siloxanes are rarely applied in pharmaceutical compositions as ingredients. The composition of the pharmaceutical preparations cited in the literature are different from the subject of the present invention, and in the pharmaceutical compositions of the state of the art, similarly to the cosmetic products, volatile siloxanes serve to obtain a good distribution on the surface of the skin.

At the same time in the present invention volatile silicone oils assure chemical and microbiological stability and good bioavailability to our composition.

The basic requirements of pharmaceutical ointments and creams containing an active ingredient are good stability, long storage time, suitable penetration of the active substance from the transdermal system, good consistency and easy application to the skin.

A disadvantage of the ointments having fatty or oily bases is that the penetration of the active ingredient is slow and the amount of the released active substance is low, because in the lipophil phase the solubility of the ointment is higher, especially in case of active substances having low aqueous solubility, and therefore, the distribution is not equal, the ointment base contains more active substance. Examples of active ingredients with low aqueous solubility are aciclovir, piroxicam, meloxicam, ibuprofen, diclofenac sodium and potassium salt, clotrimazol, bifonazol, metronidazol, nifedipin, nitroglycerin and cetirizin. Examples for creams containing the above active ingredients are Zovirax® (aciclovir), Feldene® (piroxicam), Hotemin® cream (piroxicam), Canesten® cream (clotrimazol), Mycospor® cream (bifonazol) or Rozex® cream (metranidazol).

Gel compositions containing the active ingredient in a suspended form are known from the literature, wherein the release of the active substance is adequate, but stability problems can occur during storage. These problems are caused by the chemical and microbiological reactions on the contact areas of the different surfaces, which may change the chemical condition of the active substance. These kind of stability problems can occur for example during the storage of Hotemin® cream containing piroxicam, Voltaren® emulgel (diclofenac) or Rozex® gel containing metronidazol.

OBJECT OF THE INVENTION

The aim of the present invention is to develop a pharmaceutical preparation having better bioavailability than the ointments having fatty or oily bases and some gels and also to avoid stability problems occurring during the storage of emulgels or gels containing the active substance in suspended form.

SUMMARY OF THE INVENTION

Surprisingly, it has been found that the above aims can be reached by a pharmaceutical preparation wherein volatile silicon oils are used as adjuvants. To improve the stability and penetration properties of the ointments and gels containing the above mentioned active ingredients, we used mixtures of silicone oils with different volatility in properly selected ratios.

The subject of the present invention is a transdermal preparation containing a pharmaceutically active ingredient, wherein the particles of the active ingredient are coated with highly volatile silicones or a mixture thereof and these coated particles are dispersed in a gel or cream base.

The pharmaceutical preparation of the present invention contain aciclovir, piroxicam, meloxicam, ibuprofen, diclofenac sodium and diclofenac potassium salt, clotrimazol, bifonazol, metronidazol, nifedipin, nitroglycerin or cetirizin as active ingredients; hexamethyldisiloxane and/or octamethyltrisiloxane and/or decamethylpentacyclosiloxane as volatile siloxane adjuvants; carboxyvinyl polymer, hydroxypropyl-methylcellulose or a mixture thereof as ointment bases.

A further subject of the present invention is a method for the preparation of such pharmaceutical compositions by coating the particles of the active ingredient with highly volatile silicones or a mixture thereof and the obtained mixture is dispersed in a gel or cream base, thus the particles in the gel or cream base are surrounded by silicone coating.

The essence of the invention is that the solid particles of the active ingredient incorporated in the gel are coated with volatile silicon oils, which evaporate from the surface of the skin in the course of use. The active substance and the other ingredients of the gel remain on the surface of the skin and adsorb fast through the physiological transport systems (diffusion, penetration, permeation) of the skin.

Stability can be increased with the silicone coating, which forms a so-called "third phase" in the gels. This "third phase" interacts neither with the active ingredient, nor with the other adjuvants of the gel. Silicone oils form a coating around the active ingredient particles, which protects the active ingredient from chemical and microbiological impacts assuring the pharmaceutical composition good chemical and microbiological stability.

Applying the gel to the skin the silicone compound evaporates, thus it does not have any interaction with the human organism. The particles of the active ingredients remain on the surface of the skin and release in the body. After the evaporation of the adjuvant, the active substance particles can release easier and more effectively into the layers of the skin.

The most appropriate silicon oils for coating the active ingredient of the transdermal composition of the present invention are hexamethyldisiloxane, octamethyltrisiloxane and decamethylpentacyclosiloxane.

The advantageous properties of the pharmaceutical composition of the present invention are demonstrated by the following experiments:

BRIEF DESCRIPTION OF THE DRAWINGS

FIG. 5 shows the released percentage of the active ingredient comparing to the whole amount in case of the two compositions.

FIG. 6 demonstrates the released amount of the active substance on a certain surface of the skin in mg/cm$^2$ in case of the two compositions.

FIG. 10 demonstrates the released amount of the active substance on a certain surface of the skin in $mg/cm^2$ in relation the half time of the diffusion. (Q root (t))

CHEMICAL STABILITY TEST

One of the chemical stability problems of the gel type pharmaceutical formulations containing active substance in dispersed form is caused by the reactions occurring at the contact points of the surfaces, which can lead to the change of the chemical condition of the active ingredient.

The polymorph form I of piroxicam is a white substance with crystalline structure, which turns into a bright yellow colour when dissolved in water or in other solvents. In case of traditional ointments and gels containing this active substance, the above described chemical reactions change the intensity of colour of the pharmaceutical preparation.

It has been found that contrary to the cream and gel formulations of the state of the art, the colour of the aqueous gel of the present invention containing the active ingredient coated with volatile silicone oils (hexamethyldisiloxane and/or octamethyltrisiloxane, or a mixture thereof in a ratio of 1:1) does not change. The pharmaceutical preparations of the present invention were examined with stability tests complying with the current ICH (International Conference on Harmonisation of Technical Requirements for the Registration of Pharmaceuticals for Human Use) rules, and the white colour of the preparations did not change during the experiments.

The active ingredient is coated with the volatile silicon oils in a manner that the other ingredients of the gel formulation do not have contact with the active ingredient as a result of which the preparation has good chemical stability.

Experiments for Mass Decrease

A basic requirement of good bioavailability is that the active substance should have a good release from the pharmaceutical preparation. The active ingredient of the composition of the present invention releases after the evaporation of the silicon oils serving as a coating. This process is shown by the weight decrease of the preparation. As a reference we used Hotemin® cream which is a cream with a fatty basis.

The ingredients of Hotemin® cream 1% are: methyl parahydroxybenzoate, macrogol cetylstearyl ether, sorbitan stearate, stearic acid, cetyl stearil alcohol, white vaseline, liquid paraffin, purified water.

Figure 1:
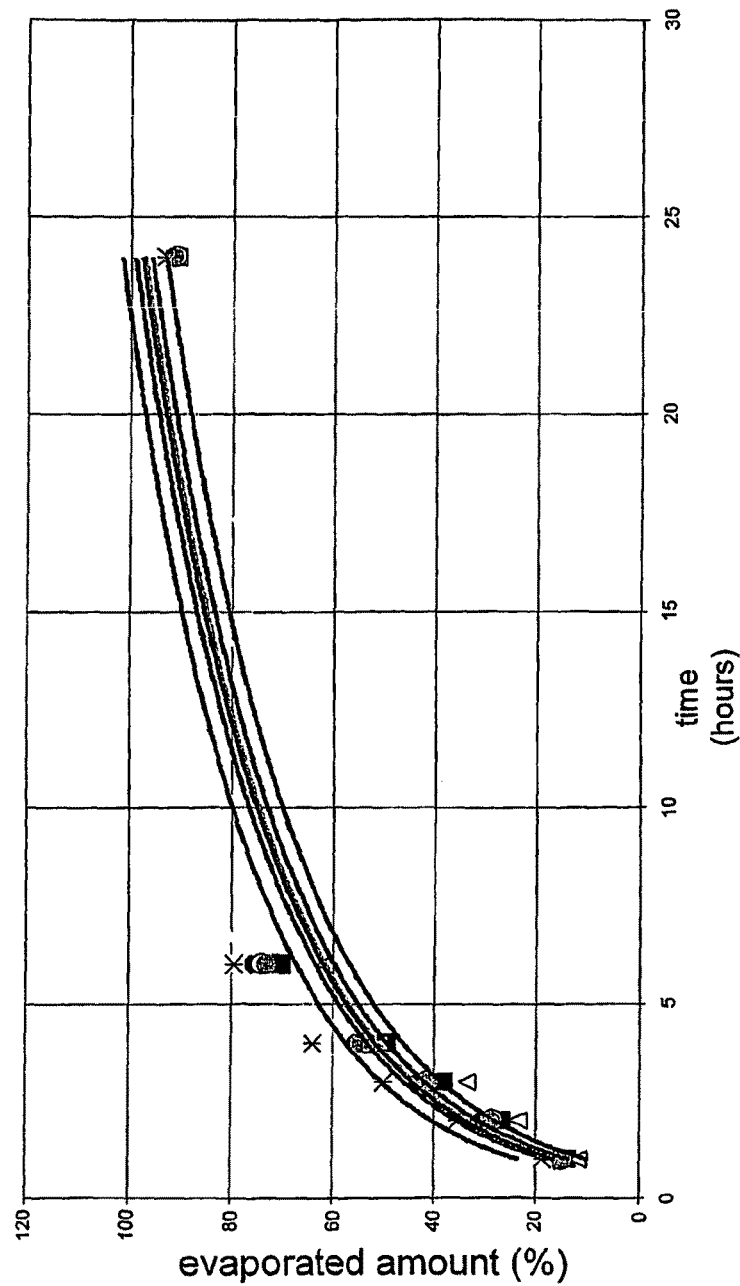
FIG. 1 demonstrates the kinetics of evaporation from silane containing system, which was studied in the mass decrease experiments. 5 samples were stored in a standard humidity exsiccator and were measured on analytical scales at certain intervals. The results of 5 measurements are demonstrated by the curves. Black pots indicate the curve demonstrating the mean value.
Figure 2:
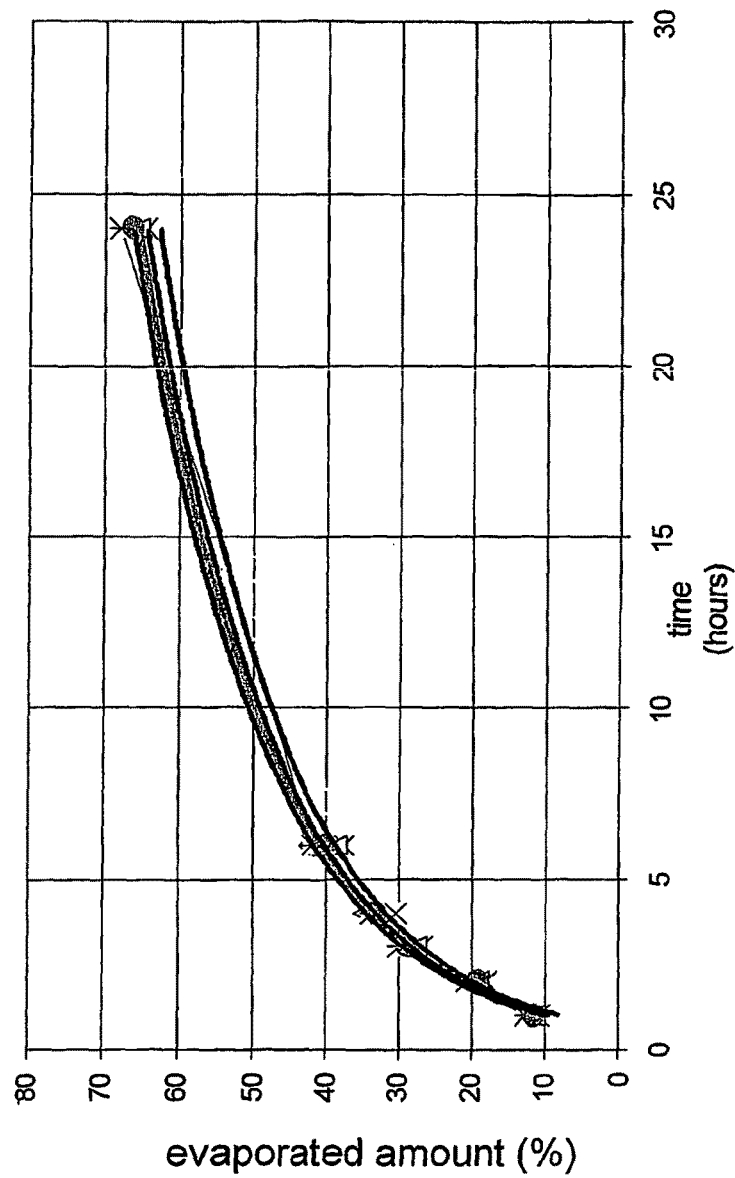
FIG. 2 demonstrates the kinetics of evaporation from silane containing system, which was studied in the mass decrease experiments. 3 samples were stored in a standard humidity exsiccator and were measured on analytical scales at certain intervals. The results of 3 measurements are demonstrated by the curves. Black pots indicate the curve demonstrating the mean value.

The samples were stored in a standard humidity exsiccator and they were measured on analytical scales at certain intervals. FIGS. 1 and 2 demonstrate the mass decrease and its relation to time.

The results of the measurements show that the evaporation is faster from the system containing the volatile silicones than from the reference preparation. After 24 hours only the active ingredient and a small amount of the polymer adjuvant remained on the scales. The reference ointment had lower mass decrease; only the 60% of the whole mass evaporated.

Experiments Concerning the Transport Through the Biological Membranes

Another basic condition of good bioavailability is the easy diffusion of the active substance after release through the biological membrane by active or passive transport.

The transport of the active ingredient through apolar and semipolar biological membranes (for example: skin) was studied with the help of an apparatus operating according to the operation principle of the vertical diffusion cell developed by the Hanson Company (Hanson Microette™ Topical & Transdermal Diffuson Cell System, Hanson Research Corporation).

The reference composition of the experiments is Hotemin® ointment.

Diffusion Through Apolar Membrane

Diffusion through apolar membrane was studied because the upper layer of the skin, the stratum corneum, has a lipophil, apolar character because of the chemical characteristics of its components. Therefore, first of all pharmacones having the ability of dissolving in the stratum corneum are able to get into it as well as the drugs which have apolar characteristics.

Figure 3:
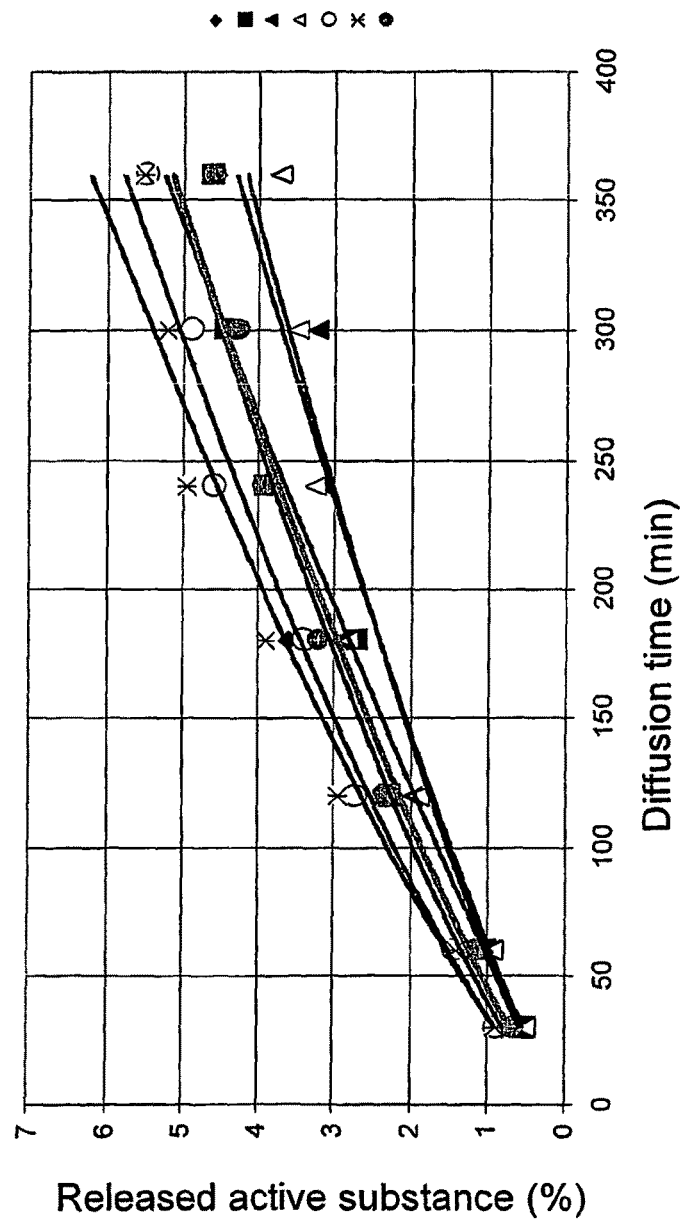
FIG. 3 relates to the release of piroxicam from the silane composition through a lipophil membrane. The results of the diffusion experiments through apolar membrane are demonstrated here. Black pots indicate the curve demonstrating the mean value of 6 measurements.

FIG. 3 shows the results of the experiments carried out using a membrane impregnated with isopropyl myristate.

Figure 4:
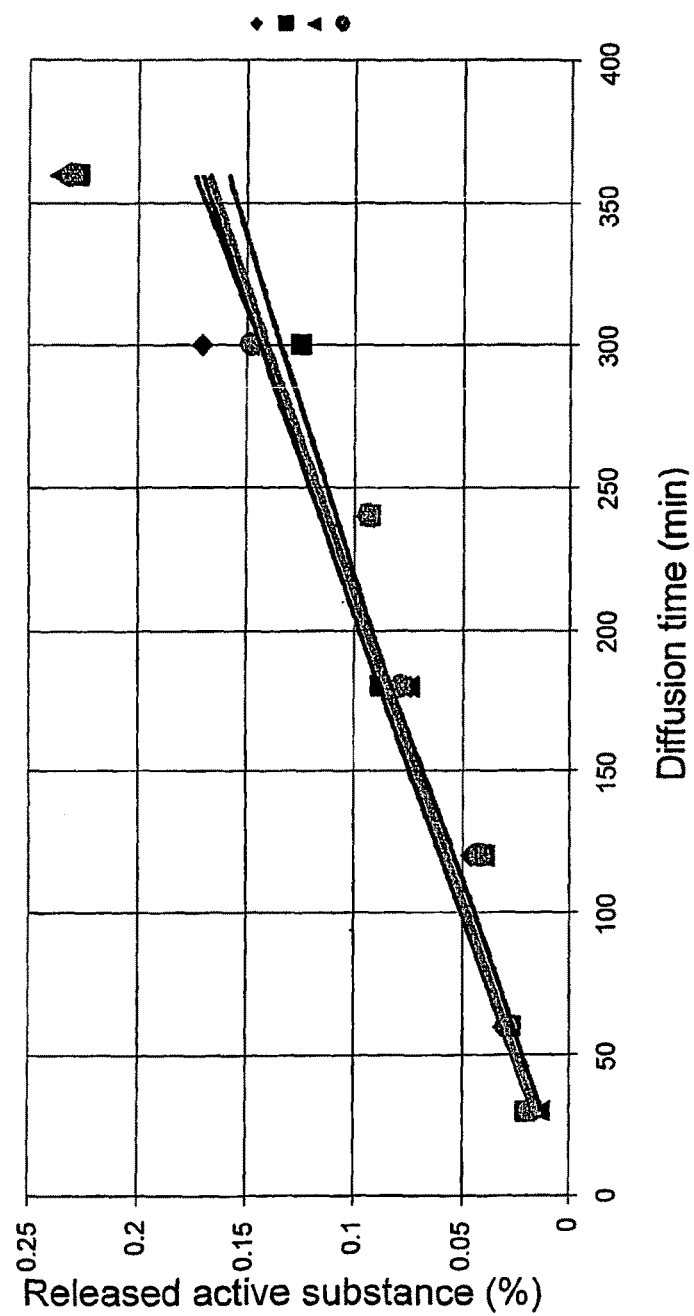
FIG. 4 relates to the release of piroxicam from Hotemin® ointment through a lipophil membrane. The results of the diffusion experiments through apolar membrane are demonstrated here. Black pots indicate the curve demonstrating the mean value of 3 measurements.
Figure 5:
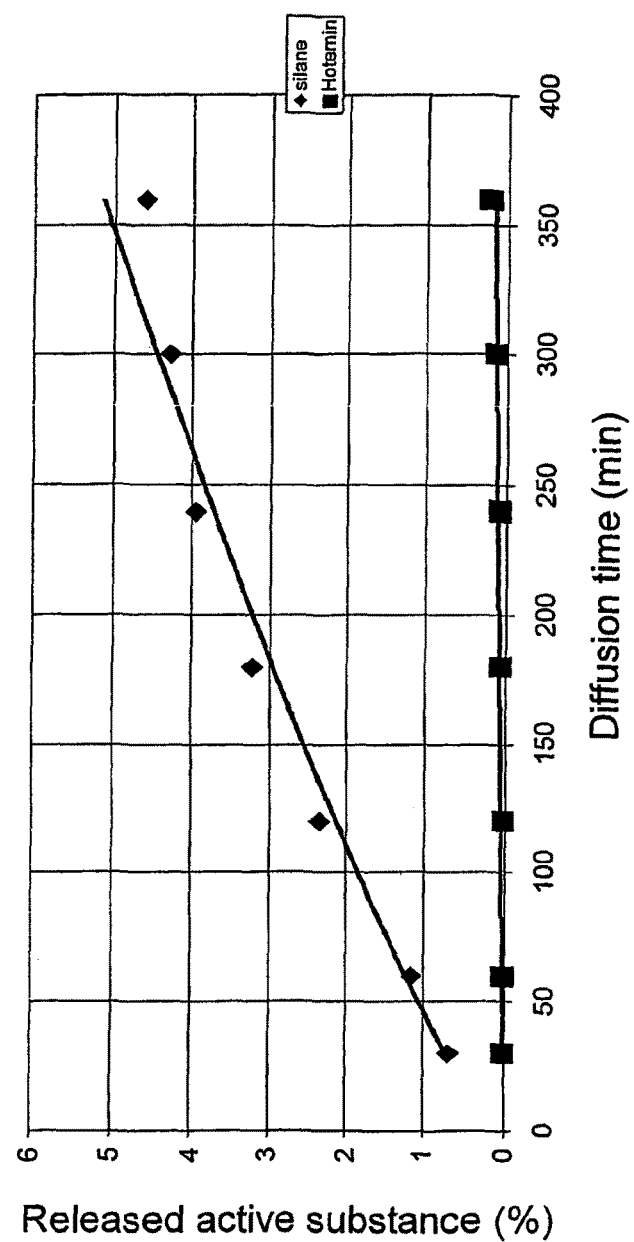
FIG. 5 relates to a comparative test, which demonstrates the release of piroxicam from silane system and from Hotemin® cream through a lipophil membrane.
Figure 6:
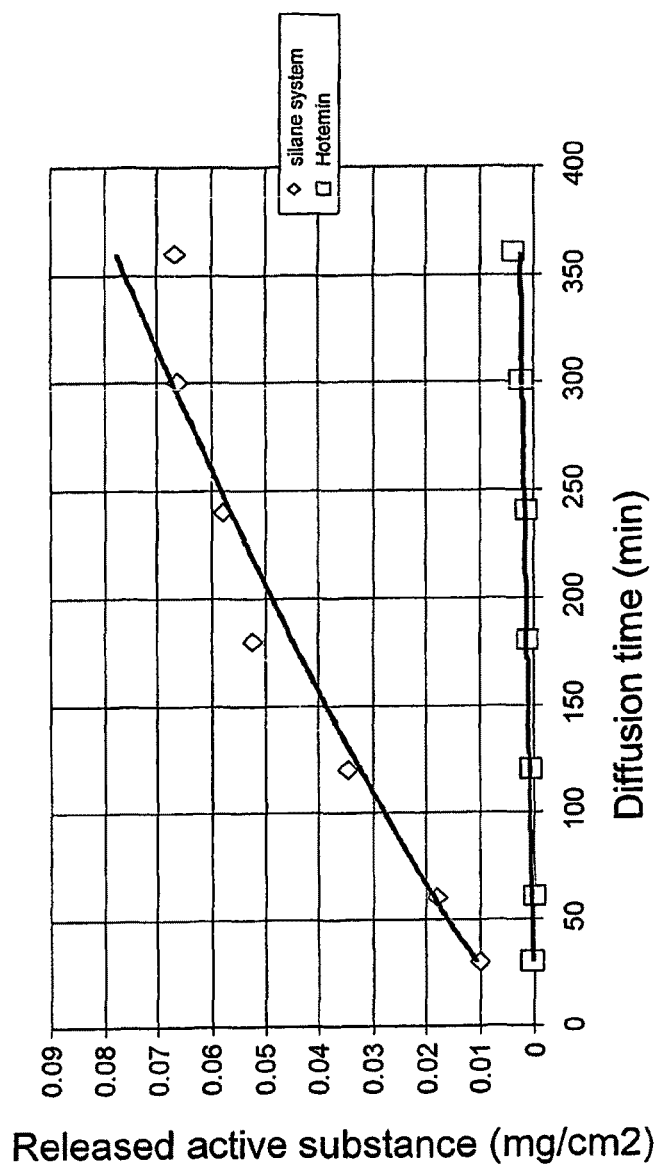
FIG. 6 relates to a comparative test, which demonstrates the release of piroxicam from silane system and from Hotemin® cream through a lipophil membrane.
Figure 7:
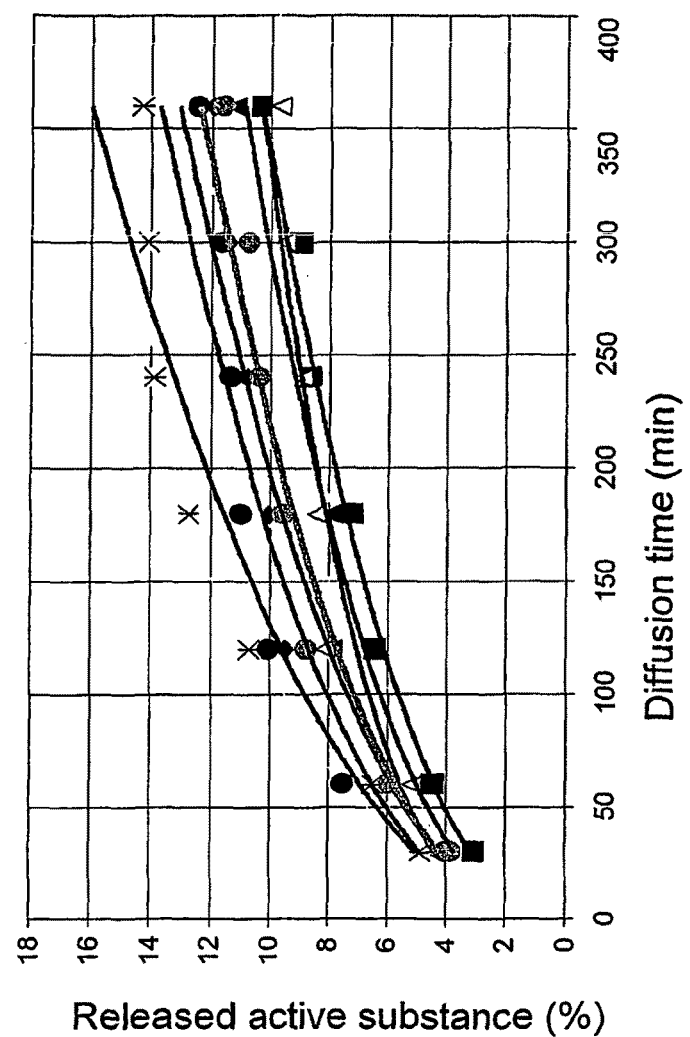
FIG. 7 relates to the release of piroxicam from the silane composition through a semipolar membrane. The results of the diffusion experiments through semipolar membrane are demonstrated here. Black pots indicate the curve demonstrating the mean value of 5 measurements.
Figure 8:
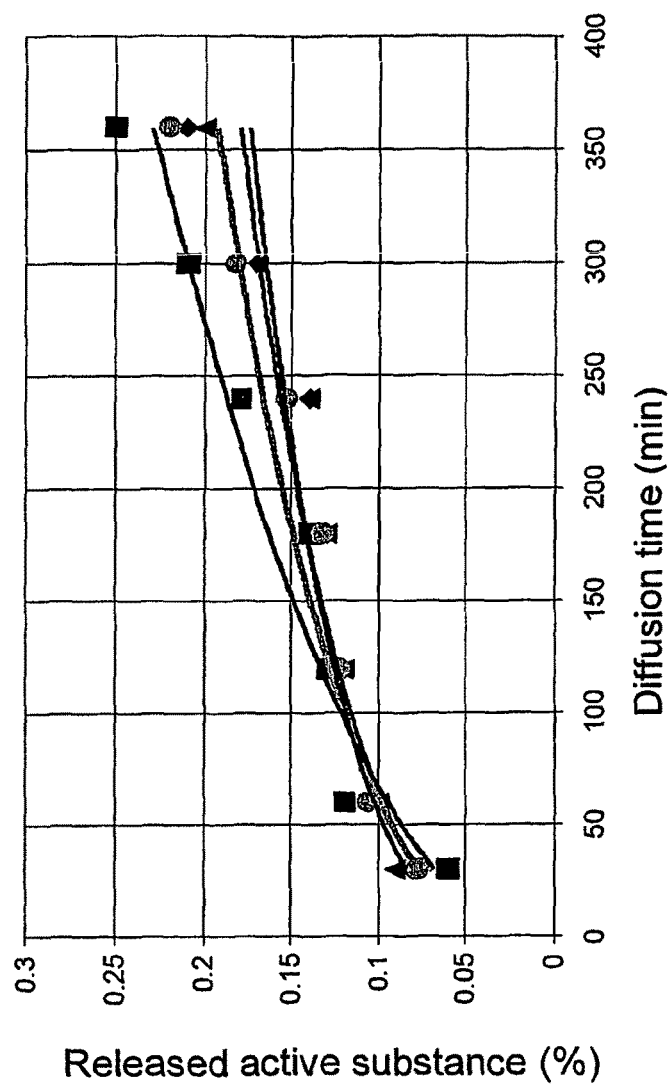
FIG. 8 relates to the release of piroxicam from Hotemin® ointment through a semipolar membrane. The results of the diffusion experiments through semipolar membrane are demonstrated here. Black pots indicate the curve demonstrating the mean value of 3 measurements.
Figure 9:
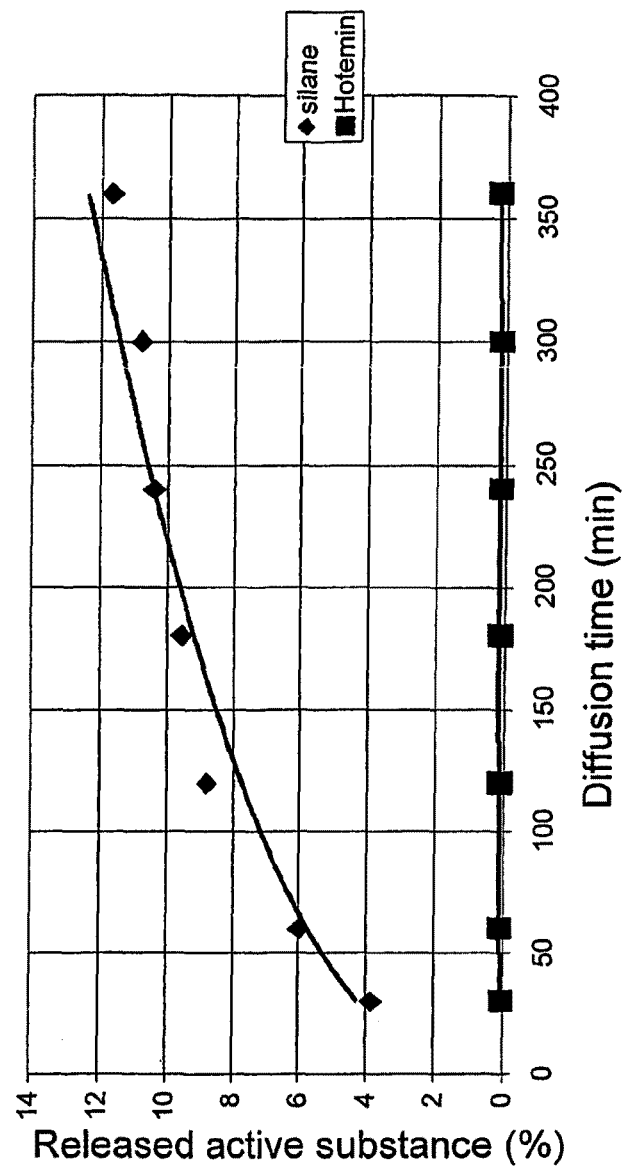
FIG. 9 relates to a comparative experiment, which demonstrates the release of piroxicam from the "silane system" and Hotemin® composition through a semipolar membrane.
Figure 10:
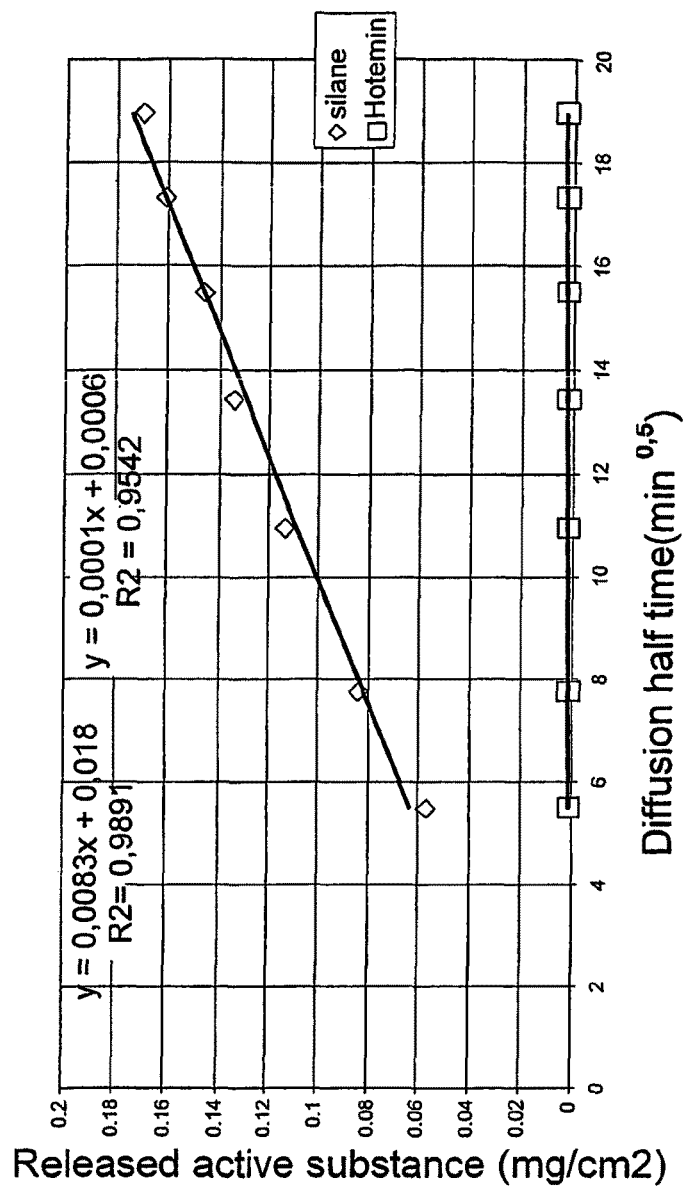
FIG. 10 relates to a comparative experiment, which demonstrates the release of piroxicam from the "silane system" and from Hotemin® composition through a semipolar membrane.

FIG. 4 demonstrates the release of the reference composition and FIGS. 5 and 6 are comparative examples.

FIG. 5 shows the released percentage of the active ingredient comparing to the whole amount and FIG. 6 demonstrates the released amount of the active substance on a certain surface of the skin in $mg/cm^2$.

Usually the process taking place in time is described with a root function. The general formula of the root function is:

$$Q = Q_0 t \quad (1),$$

wherein Q represents the released amount of the active ingredient during t time, $Q_0$ represents the released amount of the active ingredient at t=0 (it is usually 0) and m represents the gradient of the linearized function. If m is 1, the amount of the released active ingredient increases linearly in time, but usually m has a lower value than 1. When m is approximately 0.5, Q is shown by a linear function at $t_{0.5}$ function. The gradients of the linears (angular coefficient) are the velocity constant of the release.

Evaluating the functions mathematically it can be stated that the root function of equation (1) can be exactly matched to the measurement points. Table 1 shows the constant of $Q_0$, m and $R^2$ which represents the degree of the regression.

TABLE 1

The kinetics of the release of piroxicam. The constants of the root function matched to the measurement points and the values of the correlation coefficient

| Experiment No. | $Q_0$ | m | $R^2$ |
|---|---|---|---|
| Silicone containing system | | | |
| Measurement 1 | 0.061 | 0.754 | 0.982 |
| Measurement 2 | 0.025 | 0.909 | 0.986 |
| Measurement 3 | 0.039 | 0.791 | 0.973 |
| Measurement 4 | 0.031 | 0.839 | 0.979 |
| Measurement 5 | 0.069 | 0.752 | 0.994 |
| Measurement 6 | 0.063 | 0.779 | 0.984 |
| mean value | 0.047 | 0.798 | 0.988 |

TABLE 1-continued

The kinetics of the release of piroxicam. The constants of the root function matched to the measurement points and the values of the correlation coefficient

| Experiment No. | $Q_0$ | m | $R^2$ |
|---|---|---|---|
| Reference composition | | | |
| Measurement 1 | 0.0006 | 0.948 | 0.934 |
| Measurement 2 | 0.0007 | 0.927 | 0.926 |
| Measurement 3 | 0.0003 | 1.065 | 0.953 |
| mean value | 0.0005 | 0.975 | 0.945 |

The values of Table 1 show that the kinetics of the process is described precisely by the root function. The value of $Q_0$ is around 0, the value of m is between 0.5 and 1, therefore the process is not linear in time, but the velocity of the process is continuously decreasing. The root transformation was not carried out as the value of m is different from 0.5.

During the six-hour long experiment the release of the active ingredient from sample containing silicone oil was approximately 5%. From the reference composition less than 1% was released during the experiment (the maximum release of the active was approximately 0.2%).

As to the results of our experiments it can be concluded that the composition prepared according to the present invention is able to release much more of the active ingredient than the reference composition.

Diffusion Through Semipolar Membrane

The experiments of transport through a semipolar membrane gives a model of entering into the living cell, and passing through the living cell, which is a condition of the pharmacological efficacy.

The semipolar membrane was prepared by impregnating it with ethyl alcohol. The results of our experiments are demonstrated by FIGS. 7-10.

Figure 11:
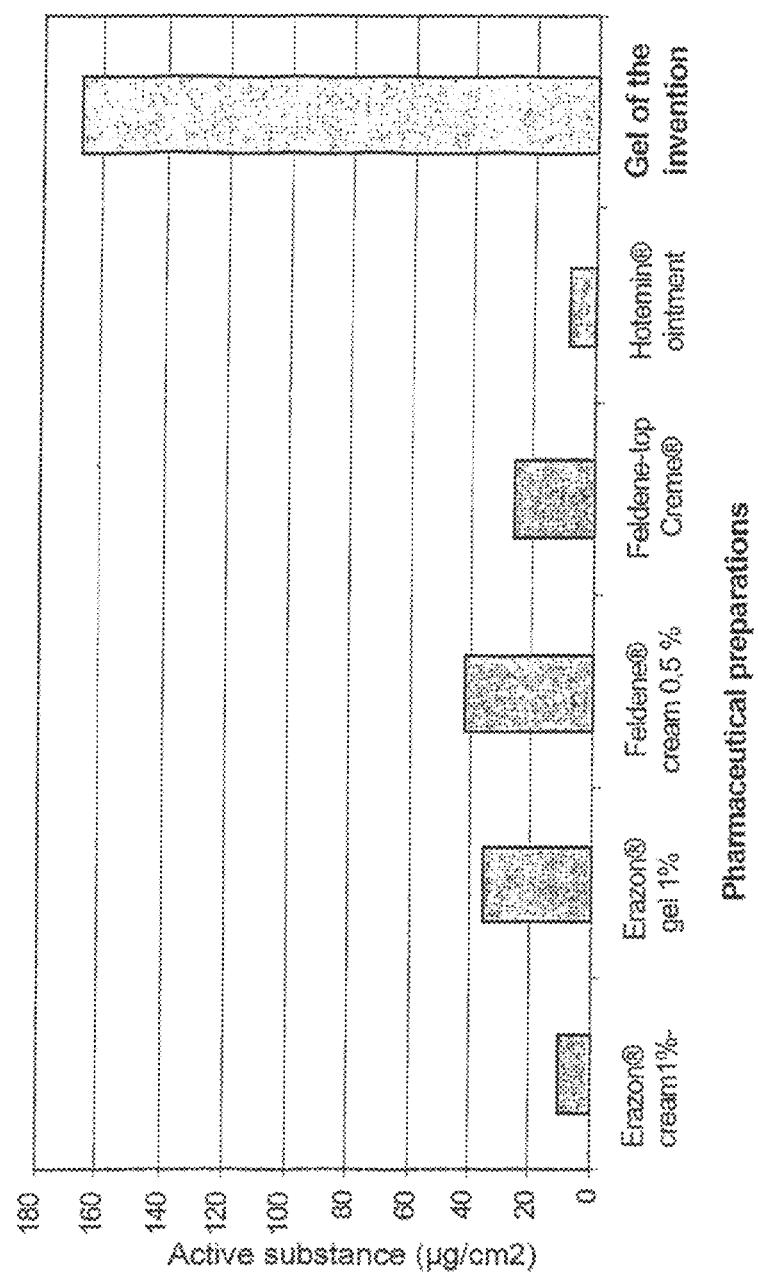
FIG. 11 relates to a comparative test, wherein the release of piroxicam from 6 different pharmaceutical preparations was studied. The diffusion time was 6 hours.

Comparing the Release of the Active Ingredients of the Composition of the Present Invention and Hotemin® Ointment:

Studying the kinetics of the process, it has been found that value m is ~0.5 of the equation (1), therefore the root transformation was carried out. The results demonstrated by FIG. 11 and the $R^2$ values of the regression line show a close match. Table 2 shows the values of $Q_0$, m and $R^2$.

TABLE 2

The release of the active ingredient through a semipolar membrane

| Experiment No. | $Q_0$ | m | $R^2$ |
|---|---|---|---|
| Silicone containing system | | | |
| Measurement 1 | 0.932 | 0.449 | 0.945 |
| Measurement 2 | 0.644 | 0.471 | 0.994 |
| Measurement 3 | 0.843 | 0.435 | 0.894 |
| Measurement 4 | 1.032 | 0.465 | 0.961 |
| Measurement 5 | 1.369 | 0.343 | 0.949 |
| Measurement 6 | 1.191 | 0.415 | 0.895 |
| mean value | 0.990 | 0.429 | 0.962 |
| Reference composition | | | |
| Measurement 1 | 0.024 | 0.340 | 0.923 |
| Measurement 2 | 0.013 | 0.494 | 0.922 |
| Measurement 3 | 0.031 | 0.249 | 0.903 |
| mean value | 0.021 | 0.373 | 0.941 |

The ratio between the composition containing silicon and the reference Hotemin® ointment is 50:1, namely the amount of the released active ingredient is fifty fold more than the released amount of the active ingredient from the reference composition.

Comparing the Release of the Active Ingredients of the Composition of the Present Invention and Other Transdermal Pharmaceutical Preparations Containing Piroxicam:

The diffusion of the composition of the present invention through a semipolar membrane was compared with the following preparations:
Erazon® 1% cream,
Erazon® 1% gel,
Feldene® 0.5% gel,
Feldene-Top Creme®,
Hotemin® ointment.

The above compositions contain piroxicam, but the carriers and the ingredients thereof are different from the composition of the invention.

It has been discovered that the release of the active ingredient from the composition containing volatile silicones is greater than the above examined creams and gels. (See FIG. 11.)

The pharmaceutical composition of the invention is further elucidated by means of the following Examples without restricting the scope of the present invention to the examples.

In the examples Silicon Fluid carriers are methylsiloxanes, namely hexamethyldisiloxane and/or octamethyltrisiloxane, or the mixtures thereof in a ratio of 1:1. In the examples the viscosity of the siloxane solutions is 0.65 cSt or 100 cSt.

EXAMPLES

Example 1

Gel Composition Containing Piroxicam as Active Ingredient:

| | |
|---|---|
| Piroxicam | 0.500 g |
| Silicone fluid 0.65 cSt | 0.500 g |
| Silicone fluid 100 cSt | 2.150 g |
| Carbopol 980 NF | 0.250 g |
| Triethanolamine | 0.200 g |
| Hydroxypropyl-methylcellulose | 1.000 g |
| Purified water | ad 50.000 g |

According to the recipe of the above example the gel was prepared in a batch size of 7 kg with a Brogtech apparatus suitable for the preparation of ointments.

1.1. Method of Preparation of the Suspension Containing the Active Ingredient:

Micronized piroxicam powder (70.0 g) is mixed with Silicone fluid 0.65 cSt (301.0 g) and Silicone fluid 100 cSt (70.0 g) in an 800 ml beaker glass, and the mixture in an Ultra-Turrax apparatus, at 4000 revs/minute for 5 minutes. The prepared suspension is stored in an airtight place until application.

1.2. Method of Preparation of the Gel Base:

Purified water (6000 g) is poured into the Brogtech apparatus and the temperature is set at 25° C. In an anchor mixer in position 4, hydroxypropyl-methylcellulose (140.0 g) is added stepwise to the mixture and it is stirred at the same revs/minute speed until total dissolution of the ointment base (approximately 1.5 hours). After dissolution Carbopol 980 NF (35.0 g) is added to the reaction mixture and it is stirred for 4 hours. The mixture is neutralized with a solution of triethanolamine (28.0 g) and purified water (100.0 g) and stirring is continued until the mixture has gel consistency.

1.3. Method of Preparation of the End Product (Drug-Gel Composition):

To the gel base prepared according to point 1.2, the suspension of the drug obtained according to point 1.1 is added stepwise, and the gel is completed to 7.00 kg with purified water. The obtained gel is homogenized for 5 minutes in the built-in homogenizer of the Brogtech apparatus at 1200 revs/min, at the maximum diameter of the slits (1.5 mm).

Example 2

Gel Composition Containing Clotrimazol as Active Ingredient:

| | |
|---|---|
| Clotrimazol | 0.200 g |
| Silicone fluid 0.65 cSt | 1.000 g |
| Silicone fluid 100 cSt | 0.200 g |
| Carbopol 980 NF | 0.100 g |
| Triethanolamine | 0.200 g |
| Hydroxypropyl-methylcellulose | 0.400 g |
| Purified water | ad 20.000 g |

According to the recipe of the above example the gel was prepared in a batch size of 7 kg with a Brogtech apparatus suitable for the preparation of ointments.

2.1. Method of Preparation of the Suspension Containing the Active Ingredient:

Micronized clotrimazol powder (70.0 g) is mixed with Silicone fluid 0.65 cSt (350.0 g) and Silicone fluid 100 cSt (70.0 g) in a 800 ml beaker glass, and the mixture is homogenized in an Ultra-Turrax apparatus, at a 4000 revs/minute for 5 minutes. The prepared suspension is stored in an airtight place until application.

2.2. Method of Preparation of the Gel Base:

Purified water (6000 g) is put into the Brogtech apparatus and the temperature is set at 25° C. In an anchor mixer in position 4, hydroxypropyl-methylcellulose (140.0 g) is added stepwise to the mixture and it is stirred at the same revs/minute speed until total dissolution of the ointment base (approximately 1.5 hours). After dissolution Carbopol 980 NF (35.0 g) to the reaction mixture and it is stirred for 4 hours. The mixture is neutralized with a solution of triethanolamine (28.0 g) and purified water (100.0 g) and stirring is continued until the mixture has gel consistency.

2.3. Method of Preparation of the End Product (Gel Composition):

To the gel base prepared according to point 2.2, the suspension of the drug obtained according to point 2.1 is added stepwise, and the gel is completed to 7.00 kg with purified water. The obtained gel is homogenized for 5 minutes in the built-in homogenizer of the Brogtech apparatus at 1200 revs/min, at the maximum diameter of the slits (1.5 mm).

Example 3

Gel Composition Containing Metranidazol as Active Ingredient:

| | |
|---|---|
| Metronidazol | 1.000 g |
| Silicone fluid 0.65 cSt | 2.000 g |
| Silicone fluid 100 cSt | 0.200 g |
| Carbopol 980 NF | 0.250 g |
| Triethanolamine | 0.200 g |
| Hydroxypropyl-methylcellulose | 0.400 g |
| Purified water | ad 20.000 g |

According to the recipe of the above example the gel was prepared in a batch size of 7 kg with a Brogtech apparatus suitable for the preparation of ointments.

3.1. Method of Preparation of the Suspension Containing the Active Ingredient:

Micronized metronidazol powder (350.0 g) is mixed with Silicone fluid 0.65 cSt (700.0 g) and Silicone fluid 100 cSt (70.0 g) in a 800 ml beaker glass, and the mixture in an Ultra-Turrax apparatus, at a 4000 revs/minute for 5 minutes. The prepared suspension is stored in an airtight place until application.

3.2. Method of Preparation of the Gel Base:

Purified water (5500 g) is put into the Brogtech apparatus and the temperature is set at 25° C. In an anchor mixer in position 4, hydroxypropyl-methylcellulose (140.0 g) is added stepwise to the mixture and it is stirred at the same revs/minute speed until total dissolution of the ointment base (approximately 1.5 hours). After dissolution Carbopol 980 NF (35.0 g) is added to the reaction mixture and it is stirred for 4 hours. The mixture is neutralized with a solution of triethanolamine (28.0 g) and purified water (100.0 g) and stirring is continued until the mixture has gel consistency.

3.3. Method of Preparation of the End Product (Gel Composition):

To the gel base prepared according to point 3.2, the suspension of the drug obtained according to point 3.1 is added stepwise, and the gel is completed to 7.00 kg with purified water. The obtained gel is homogenized for 5 minutes in the built-in homogenizer of the Brogtech apparatus at 1200 revs/min, at the maximum diameter of the gaps (1.5 mm). The obtained gel is stored in an airtight place or put into an airtight packaging (metal tube).

Example 4

Gel Composition Containing Cetirizin as Active Ingredient:

| | |
|---|---|
| Cetirizin | 0.200 g |
| Menthol | 0.200 g |
| Ethyl alcohol | 0.200 g |
| Silicone fluid 0.65 cSt | 1.000 g |
| Silicone fluid 100 cSt | 0.200 g |
| Carbopol 980 NF | 0.250 g |
| Triethanolamine | 0.200 g |
| Purified water | ad 20.000 g |

According to the recipe of the above example the gel was prepared in a batch size of 7 kg with a Brogtech apparatus suitable for the preparation of ointments.

4.1. Method of Preparation of the Suspension Containing the Active Ingredient:

Micronized cetirizin powder (70.0 g) is mixed with Silicone fluid 0.65 cSt (350.0 g) and Silicone fluid 100 cSt (70.0 g) in an 800 ml beaker glass, and the mixture is homogenized in an Ultra-Turrax apparatus, at a 4000 revs/minute for 5 minutes. The prepared suspension is stored in an airtight place until application.

4.2. Method of Preparation of the Menthol Solution:

Menthol (70.0 g) is dissolved in ethyl alcohol in a 300 ml beaker glass. It is stored airtight until utilization.

4.3. Method of Preparation of the Gel Base:

Purified water (6000 g) is poured into the Brogtech apparatus and the temperature is set at 25° C. In an anchor mixer in position 4, hydroxypropyl-methylcellulose (140.0 g) is added stepwise to the mixture and it is stirred at the same revs/minute speed until total dissolution of the ointment base (approximately 1.5 hours). After dissolution Carbopol 980 NP (35.0 g) to the reaction mixture and it is stirred for 4 hours. The mixture is neutralized with a solution of triethanolamine (28.0 g) and purified water (100.0 g) and stirring is continued until the mixture has a gel consistency.

4.3. Method of Preparation of the End Product (Gel Composition):

To the gel base prepared according to point 4.2, the suspension of the drug obtained according to point 4.1 is added stepwise, and the gel is completed to 7.00 kg with purified water. The obtained gel is homogenized for 5 minutes in the built-in homogenizer of the Brogtech apparatus at 1200 revs/min, at the maximum diameter of the slits (1.5 mm). The obtained gel is stored in an airtight place or put into an airtight packaging (metal tube).

The invention claimed is:

1. A pharmaceutical composition in gel or cream form for transdermal administration of a pharmaceutically active ingredient, comprising:
   a multiplicity of particles of an active pharmaceutical ingredient;
   a highly volatile silicone or a mixture of highly volatile silicones coated on the multiplicity of particles of an active pharmaceutical ingredient, the particles coated with the highly volatile silicone or mixture of highly volatile silicones prior to addition to the composition;
   a hydrated gel or cream base, in which the multiplicity of particles of the active pharmaceutical ingredient, coated with the highly volatile silicone or mixture of highly volatile silicones, are dispersed;
   wherein the coating of highly volatile silicone or mixture of highly volatile silicones substantially prevents contact between the active pharmaceutical agent and the remainder of the pharmaceutical composition at least until application; and
   wherein a mass ratio of the highly volatile silicone or the mixture of highly volatile silicones to the active pharmaceutical ingredient is about 2:1 or greater.

2. The pharmaceutical composition of claim 1 wherein the pharmaceutically active ingredient is selected from the group consisting of acyclovir, piroxicam, meloxicam, ibuprofen, diclofenac sodium or potassium, clotrimazol, bifonazol, metronidazol, nifedipin, nitroglycerine and cetirizin.

3. The pharmaceutical composition of claim 1 wherein the highly volatile silicone or mixture of highly volatile silicones is selected from the group consisting of hexamethyldisiloxane, octamethyltrisiloxane, decamethylpentacyclosiloxane and mixtures thereof.

4. The pharmaceutical composition of claim 1 wherein the hydrated gel or cream base is selected from the group consisting of hydrated carboxyvinyl polymer, hydrated hydroxypropyl-methyl cellulose and mixtures thereof.

5. The pharmaceutical composition of claim 1 wherein the pharmaceutically active ingredient is diclofenac sodium or potassium.

6. The pharmaceutical composition of claim 1, wherein the highly volatile silicone or mixture of highly volatile silicones comprises hexamethyldisiloxane.

7. The pharmaceutical composition of claim 1, wherein the hydrated gel or cream base comprises hydrated carboxyvinyl polymer.

8. The pharmaceutical composition of claim 1, wherein the application comprises application to the surface of the skin.

9. The pharmaceutical composition of claim 1, further comprising a menthol.

10. The pharmaceutical composition of claim 1, wherein the mass ratio is between about 2:1 and about 6:1.

11. The pharmaceutical composition of claim 1, wherein the mass ratio is between about 2:1 and about 5:1.

12. The pharmaceutical composition of claim 1, wherein the mass ratio is about 6:1 or greater.

13. The pharmaceutical composition of claim 1, where a mixture of highly volatile silicones is coated on the multiplicity of particles of an active pharmaceutical ingredient.

14. A pharmaceutical composition of claim 13, wherein the mixture of highly volatile silicones comprises at least a first silicone and a second silicone, and the first silicone has a viscosity of 0.65 cSt.

15. A pharmaceutical composition of claim 14, wherein the weight ratio of the first silicone to the second silicone ranges from 1:4.3 to 10:1.

16. A pharmaceutical composition of claim 13, wherein the highly volatile silicone or mixture of highly volatile silicones comprises hexamethyldisiloxane.

17. A pharmaceutical composition of claim 14, wherein the highly volatile silicone or mixture of highly volatile silicones comprises hexamethyldisiloxane.

18. A pharmaceutical composition of claim 15, wherein the highly volatile silicone or mixture of highly volatile silicones comprises hexamethyldisiloxane.

19. A pharmaceutical composition of claim 13, wherein the hydrated gel or cream base comprises hydrated carboxyvinyl polymer.

20. A pharmaceutical composition of claim 14, wherein the hydrated gel or cream base comprises hydrated carboxyvinyl polymer.

21. A pharmaceutical composition of claim 15, wherein the hydrated gel or cream base comprises hydrated carboxyvinyl polymer.

22. A pharmaceutical composition of claim 13, wherein the application comprises application to the surface of the skin.

23. A pharmaceutical composition of claim 14, wherein the application comprises application to the surface of the skin.

24. A pharmaceutical composition of claim 15, wherein the application comprises application to the surface of the skin.

25. A pharmaceutical composition of claim 13, further comprising a menthol.

26. A pharmaceutical composition of claim 14, further comprising a menthol.

27. A pharmaceutical composition of claim 15, further comprising a menthol.

28. A pharmaceutical composition of claim 13, wherein the mass ratio is between about 2:1 and about 6:1.

29. A pharmaceutical composition of claim 14, wherein the mass ratio is between about 2:1 and about 6:1.

30. A pharmaceutical composition of claim 15, wherein the mass ratio is between about 2:1 and about 6:1.

31. A pharmaceutical composition of claim 13, wherein the mass ratio is between about 2:1 and about 5:1.

32. A pharmaceutical composition of claim 14, wherein the mass ratio is between about 2:1 and about 5:1.

33. A pharmaceutical composition of claim 15, wherein the mass ratio is between about 2:1 and about 5:1.

34. A pharmaceutical composition of claim 13, wherein the mass ratio is about 6:1 or greater.

35. A pharmaceutical composition of claim 14, wherein the mass ratio is about 6:1 or greater.

36. A pharmaceutical composition of claim 15, wherein the mass ratio is about 6:1 or greater.

* * * * *

UNITED STATES PATENT AND TRADEMARK OFFICE
CERTIFICATE OF CORRECTION

PATENT NO. : 9,775,908 B2
APPLICATION NO. : 12/672696
DATED : October 3, 2017
INVENTOR(S) : Endre Mikulásik et al.

Page 1 of 1

It is certified that error appears in the above-identified patent and that said Letters Patent is hereby corrected as shown below:

In the Drawings

Sheet 10 of 11 (X-axis, Figure 10) at Line 1 (approx.), Change "(min $^{0,5}$)" to --(min $^{0.5}$)--.

Sheet 11 of 11 (X-axis, Figure 11) at Line 2 (approx.), Change "0,5 %" to --0.5 %--.

In the Specification

In Column 2 at Line 2, Change "malting" to --making--.

In Column 3 at Line 8, Change "(metranidazol)." to --(metronidazol).--.

In Column 5 at Line 58, Change "stearil" to --stearyl--.

In Column 6 at Line 15 (approx.), Change "Diffuson" to --Diffusion--.

In Column 6 at Lines 23-24 (approx.), Change "pharmacones" to --pharmaconex--.

In Column 9 at Line 59, Change "Metranidazol" to --Metronidazol--.

In Column 11 at Line 8, Change "NP" to --NF--.

In the Claims

In Column 11 at Line 49, In Claim 2, change "nitroglycerine" to --nitroglycerin--.

Signed and Sealed this
Thirteenth Day of February, 2018

Andrei Iancu
*Director of the United States Patent and Trademark Office*